United States Patent [19]

Amedro et al.

[11] 4,413,231

[45] Nov. 1, 1983

[54] EDDY CURRENT INSPECTION PROBE FOR NON-DESTRUCTIVE INSPECTION OF TUBES WITH A PROBE BODY HAVING AN OUTER COILED SPRING SHEATH AND AN INNER PLASTIC MATERIAL SHEATH

[75] Inventors: Albert Amedro; Bernard Audemard; René De Mul, all of Paris, France

[73] Assignee: Compagnie Generale de Radiologie, Paris, France

[21] Appl. No.: 169,779

[22] Filed: Jul. 17, 1980

[30] Foreign Application Priority Data

Jul. 24, 1979 [FR] France ............................. 79 19080

[51] Int. Cl.³ ...................... G01N 27/72; G01N 27/82
[52] U.S. Cl. .................................... 324/220; 174/136
[58] Field of Search ............................. 324/219–221; 174/136

[56] References Cited

U.S. PATENT DOCUMENTS 4,153,875 5/1979 Pigeon et al. ..................... 324/220
4,196,390 4/1980 Pitkin ................................. 324/262
4,303,884 12/1981 Malick .............................. 324/220

OTHER PUBLICATIONS

Cecco, "Design ... Eddy Current Probe ...", 12/1979, Materials Evaluation, vol. 37, No. 13, pp. 51–58.

Primary Examiner—Gerard R. Strecker
Assistant Examiner—Walter E. Snow

[57] ABSTRACT

The invention relates to a flexible probe for non-destructive inspection of long tubes.

The measuring head is connected to the electrical connection by means of a body constituted by a sheath, whose particular characteristic is that it has a limited elongation strain and a low degree of deformation on compression, so that it does not deform either during the introduction of the probe into the tube or during its extraction from the tube, no matter what the tube length.

The invention is more particularly applicable to the inspection for faults within long tubes by the eddy current method.

1 Claim, 3 Drawing Figures

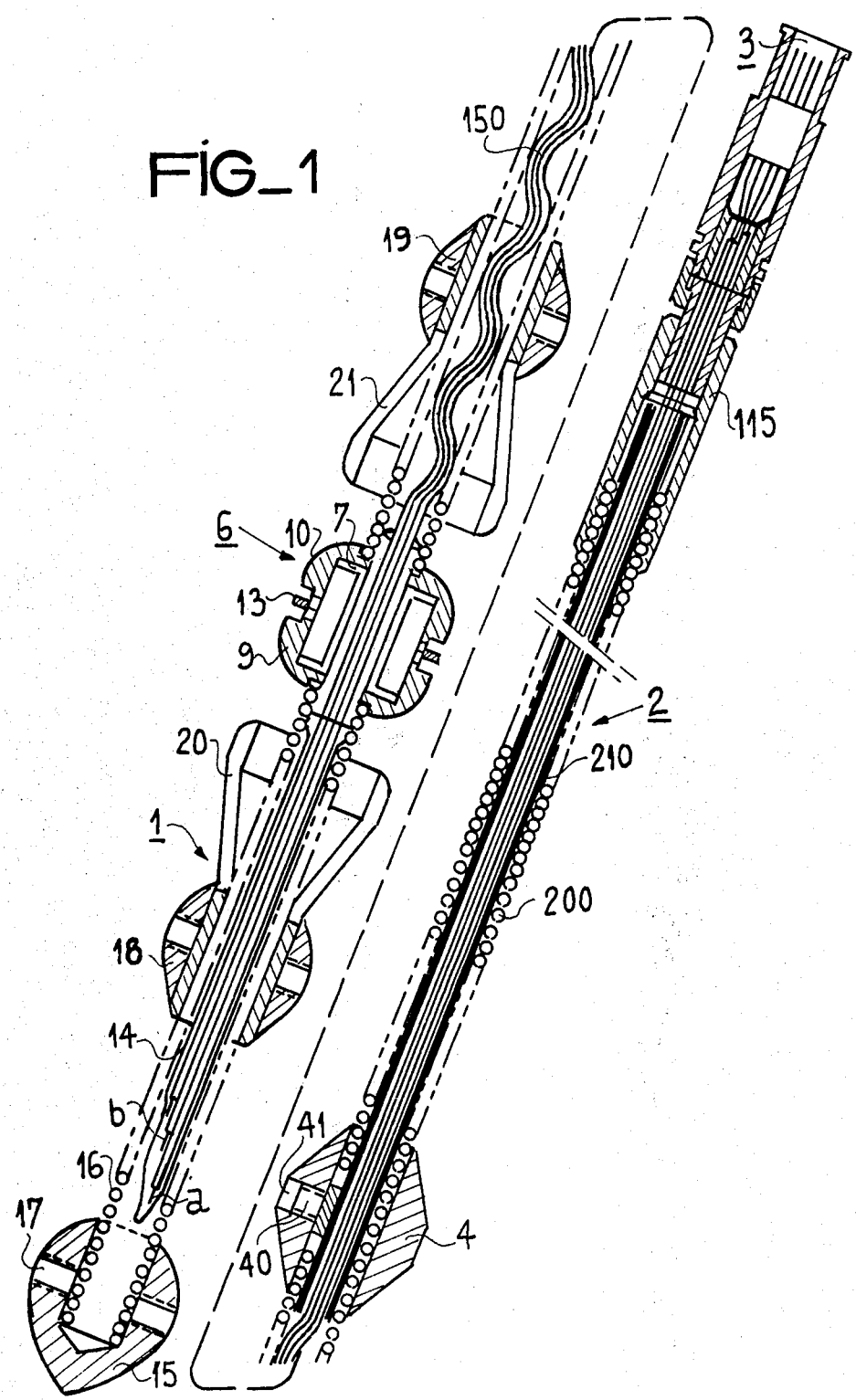

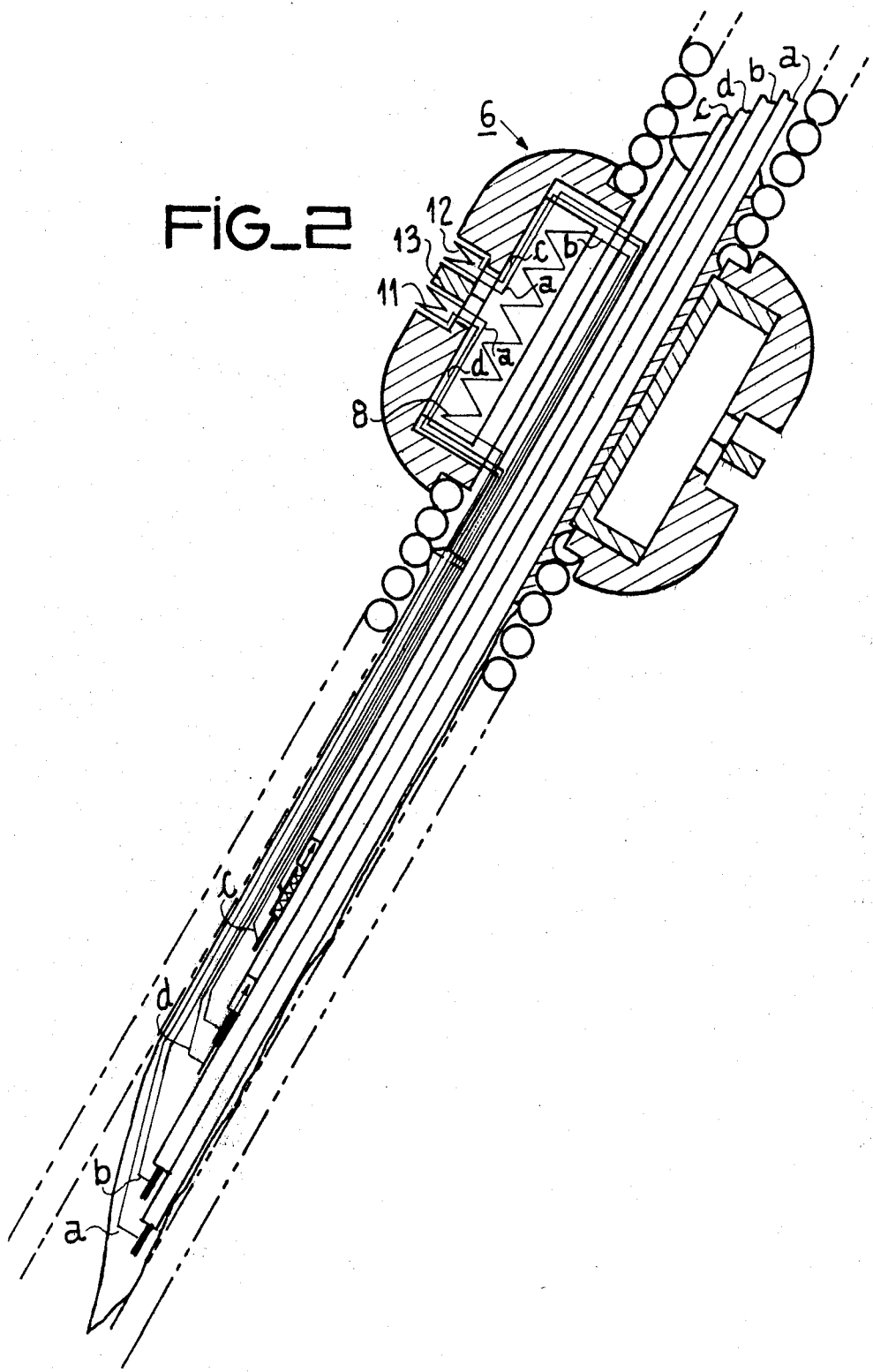

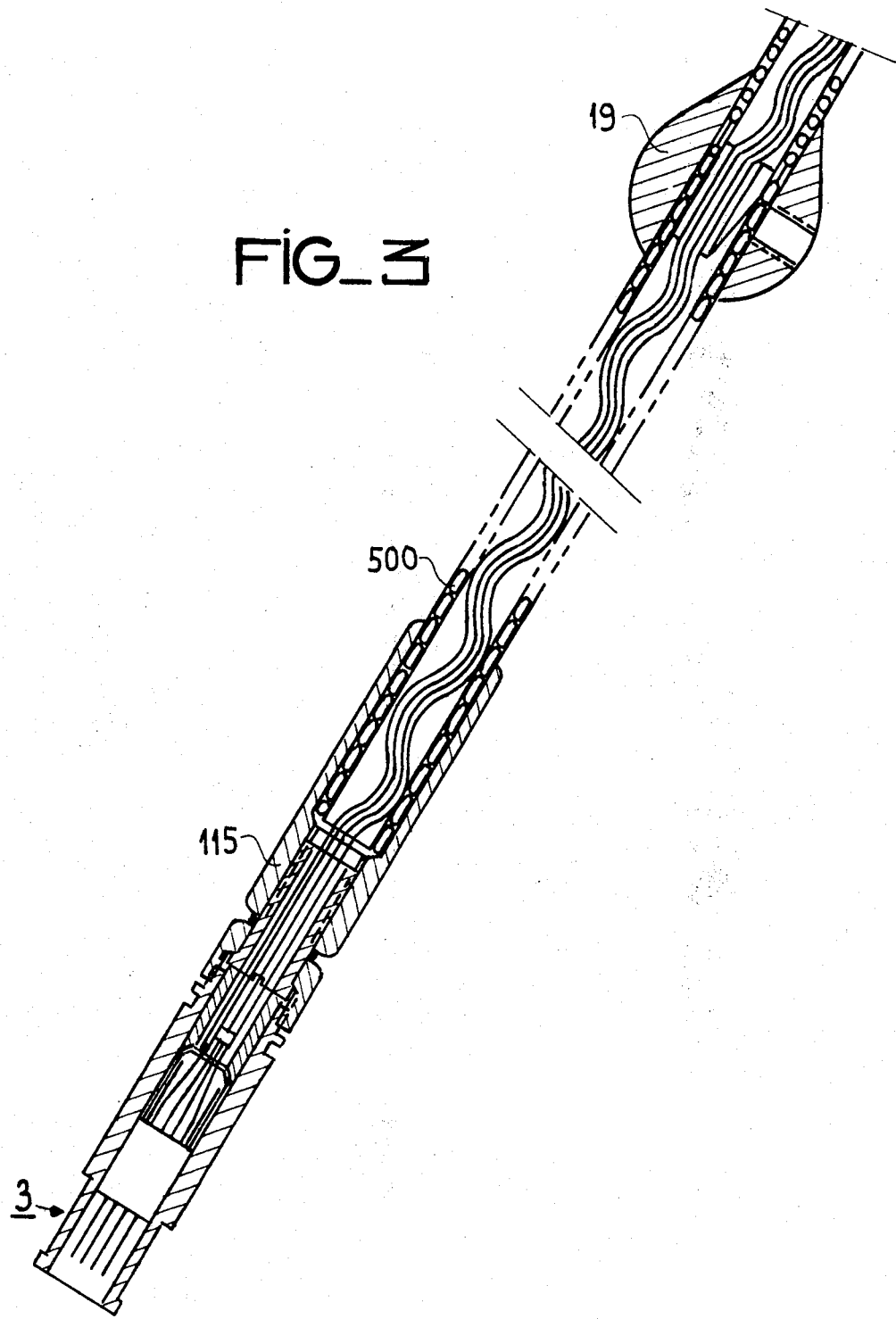

EDDY CURRENT INSPECTION PROBE FOR NON-DESTRUCTIVE INSPECTION OF TUBES WITH A PROBE BODY HAVING AN OUTER COILED SPRING SHEATH AND AN INNER PLASTIC MATERIAL SHEATH

BACKGROUND OF THE INVENTION

The invention relates to a flexible probe for the non-destructive inspection of long tubes. It more particularly relates to such a probe for carrying out inspections or controls by the so-called Eddy current method at one or more frequencies.

A probe of this type constitutes a means permitting the introduction of a pick-up or measuring head into the tube to be inspected and the transmission of the signal supplied by the said pick-up indicating the absence or presence of a defect. The pick-up is positioned in the front portion of the probe which has to advance within the tube over the entire length of the latter, no matter what the geometry and in particular the length or curvature thereof.

When the tube length exceeds a certain size the presently known probes must be injected by means of compressed air. This is difficult to perform, particularly when the tubes are curved. In fact, for certain applications where the presence of compressed air constitutes a pollution hazard which must be avoided it is proscribed.

BRIEF SUMMARY OF THE INVENTION

The present invention is directed at obviating these disadvantages and relates to a flexible probe equipped at its front end with a pick-up which detects by the Eddy current method any anomaly in the construction of the tubes. It more specifically relates to a flexible probe for the non-destructive inspection of long tubes, wherein it comprises a member constituted by a sheath having both a limited elongation strain and a limited degree of deformation on compression, connecting a measuring head to an electrical connection.

DESCRIPTION OF THE DRAWINGS AND PREFERRED EMBODIMENTS

The invention is described in greater detail hereinafter relative to non-limitative embodiments and the attached FIGS. 1 to 3 which diagrammatically illustrate two embodiments of a flexible probe according to the invention. For reasons of clarity the same components carry the same references throughout the drawings.

As shown in FIGS. 1 and 2 (FIG. 2 constituting an enlarged detail of FIG. 1) a probe according to the invention is essentially in three parts, namely the actual measuring head 1, the probe body 2 and the connection 3. These parts are interconnected by first and second connecting members 4 and 115.

The measuring head, certain of whose parts are clearly visible in FIG. 2, comprises a conventional pick-up 6 incorporating the active elements of said head. It more particularly comprises a shaft 7, for example of stainless steel on which is positioned a saturation coil 8 and two half-shells 9 and 10 in which are inserted external coils 11 and 12, separated from one another by a separating ring 13. These coils are connected to supply cables a, b, c, and d, by connections made in staircase-like manner in the front part of the probe. As a result these connections can easily be produced and are reliable. All the connections and cables are covered with a flexible insulating material, such as a silicone elastomer 14. On the probe tip is positioned a guide bush 15 locked on the protective sheaths 16 for the measuring head, which is a spring having continuous round turns giving it a certain flexibility. This bush 15 is made integral with sheath 16 by means, for example, of at least one screw introduced into thread 17. In order to better guide and centre said measuring head two centring bushes 18 and 19, each fixed to a "tulip" 20 and 21 with "petals" made from a flexible material are provided on either side of the pick-up 6. A flexible connecting zone 150 is provided between the measuring head 1 and the actual body 2. This zone 150 is fixed to body 2 by means of a first connecting member 4.

According to the invention the essential characteristic of body 2 is that it has both a limited elongation strain, i.e. the strain which it undergoes during the extraction of the probe from the tube on completing the inspection operation and also a limited degree of deformation on compression, i.e. the strain which it may undergo during the introduction of the probe into the tube. This strain increases with decreasing diameter and increasing length dimensions of the tubes or if the latter have profiles with small radii of curvature.

In a first constructional variant shown in FIGS. 1 and 2 body 2 comprises a sheath incorporating the combination of a first external sheath 200 with round contiguous turns and a second internal sheath 210, made from a plastics material and having a limited elongation strain co-efficient. Thus, throughout the introduction phase of the probe into tube to be inspected the external compression-resisting sheath prevents any excessive deformation. In the same way during the extraction phase of the probe from the tube, the plastics material sheath prevents any elongation of the assembly, thus preventing any risk of deterioration of the probe. Such a combination makes it possible to obviate the use of compressed air, even for the inspection of vertical tubes, because the sheath ensures an adequate rigidity for the advance of the probe using a known mechanical driving means. The front of body 2 is connected to the connecting zone 150, which is itself fixed to pick-up 6, by means of a first connecting member 4. The latter is in the form of an envelope provided with a thread 40 for receiving a screw, the whole assembly being plugged with araldite. This is a non-limitative embodiment of the connecting member. From the rear it is connected to the electrical connection 3 by means of a second connecting member 115 in the form of an envelope welded by araldite to the two parts to be connected.

In a second variant the body 2 of the probe of FIG. 3 is produced by means of a sheath constituted solely by a spring having contiguous planar turns 500. Such a configuration gives the said body the characteristic defined hereinbefore. It has both a limited elongation strain and a low degree of deformation on compression. The other members of the probe described hereinbefore co-operate with said body to permit access over the entire length of the tube being inspected to the measuring head integral therewith. Body 2 is connected to the front part of the probe by a first connecting member which, in this variant, is constituted by the centring bush 19, as well as to the connection 3 by a second connecting member 115.

The probe according to the invention has numerous applications. It is particularly well suited to the non-destructive control of small diameter and very long tubes, which in certain areas have very small radii of curvature. This is the case, for example, with U-shaped tubes having very long legs.

What is claimed is:

1. An eddy current inspection probe for the non-destructive inspection of long tubes, said probe comprising: a measuring head, a probe body and connecting members, said probe body comprising a first, outer sheath constituted by a spiral spring having round contiguous turns, a second, inner sheath made from a plastic material having a low elongation strain co-efficient and cooperating with said first sheath in such a way that during the introduction of the probe into the tube to be inspected said first outer sheath has a limited deformation, while during the extraction of the probe from the tube, after an inspection, the second, inner sheath opposes any risk of elongation.

* * * * *